Figure 4:
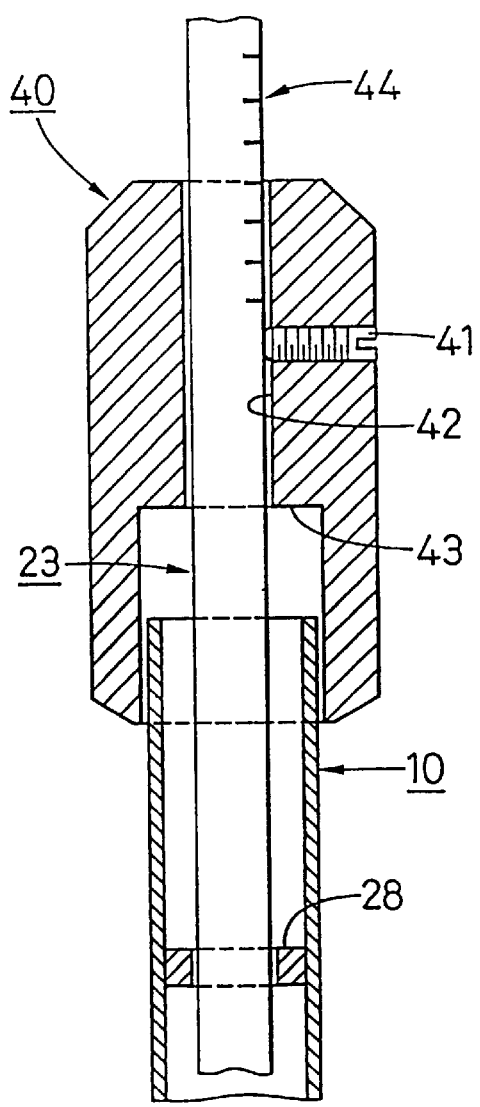

United States Patent [19]
Zech et al.

[11] Patent Number: 6,110,178
[45] Date of Patent: Aug. 29, 2000

[54] APPARATUS FOR THE PRODUCTION OF ENDOCHONDRAL OR OSTEOCHONDRAL BORES

[75] Inventors: Manfred Zech, Andelfingen; Werner Müller-Glauser, Wiesendangen; Christoph Saager, Frieswil; Pierre Mainil-Varlet, Bern, all of Switzerland

[73] Assignee: Sulzer Orthopadie AG, Baar, Switzerland

[21] Appl. No.: 09/202,695

[22] PCT Filed: Apr. 21, 1998

[86] PCT No.: PCT/CH98/00154

§ 371 Date: Dec. 17, 1998

§ 102(e) Date: Dec. 17, 1998

[87] PCT Pub. No.: WO98/48707

PCT Pub. Date: Nov. 5, 1998

[30] Foreign Application Priority Data

Apr. 25, 1997 [CH] Switzerland .............. 0973/97

[51] Int. Cl.⁷ .................................................. A61B 17/16
[52] U.S. Cl. .................................................. 606/96
[58] Field of Search .................. 606/80, 96, 98

[56] References Cited

U.S. PATENT DOCUMENTS

| | | | |
|---|---|---|---|
| 4,450,834 | 5/1984 | Fischer | 606/96 |
| 5,180,388 | 1/1993 | DiCarlo | 606/96 |
| 5,207,681 | 5/1993 | Ghadjar et al. | 606/96 |
| 5,409,493 | 4/1995 | Greenberg | 606/96 |
| 5,658,305 | 8/1997 | Baker | 606/80 |
| 5,667,509 | 9/1997 | Westin | 606/96 |
| 5,669,915 | 9/1997 | Caspar et al. | 606/96 |
| 5,676,545 | 10/1997 | Jones | 606/80 |
| 5,810,828 | 9/1998 | Lightman et al. | 606/80 |
| 5,888,034 | 3/1999 | Greenberg | 606/96 |

FOREIGN PATENT DOCUMENTS

| | | | |
|---|---|---|---|
| 3800482 | 7/1989 | Germany | 606/96 |
| 1448111 | 9/1976 | United Kingdom | 606/96 |

*Primary Examiner*—Paul J. Hirsch
*Attorney, Agent, or Firm*—Townsend and Townsend and Crew LLP

[57] ABSTRACT

The apparatus for the production of endochondral or osteochondral bores comprises a combination of a substantially hollow cylindrical sleeve (10), of which one end is formed as a circular cutting edge (11), with a flat borer (20) which is rotatably and axially displaceably arranged in the sleeve (10). Through pressing in of the cutting edge (11) into the tissue, advantageously only into the cartilage tissue, a tissue column is punched out which then is cut away and removed through screwing in of the flat borer (20). In this the boring is done up to the depth of the cutting edge (11) or deeper.

19 Claims, 2 Drawing Sheets

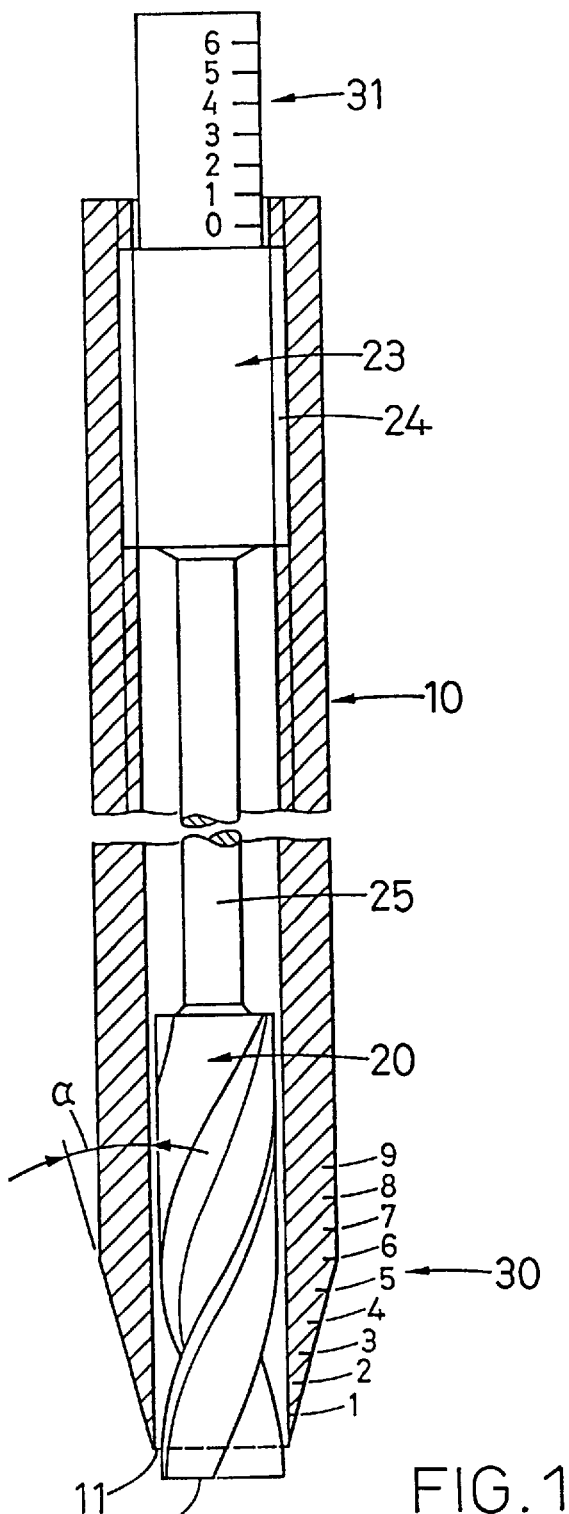
FIG. 1
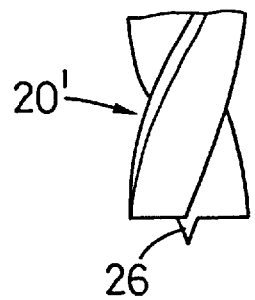
FIG. 2
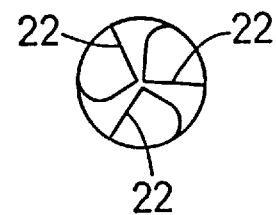
FIG. 3
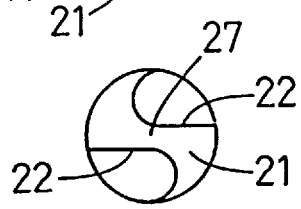

APPARATUS FOR THE PRODUCTION OF ENDOCHONDRAL OR OSTEOCHONDRAL BORES

The invention lies in the field of medical technology and relates to an apparatus in accordance with the preamble of the first patent claim for the production of endochondral and of osteochondral bores.

The most diverse artificial implants and implants which are cultivated in vitro are known by means of which defects in joint cartilages or in joint cartilages and the bone tissue lying therebelow can be repaired. Implants of this kind are for example deformable masses or pastes which are spread into the defects and which substantially adapt to any shape of defect, but which however in most cases do not have sufficient mechanical stability in order that they can be stressed immediately after the operation.

Implants are also known which have mechanical properties which are at least similar to those of natural cartilage or bone respectively. Implants of this kind have the advantage that they can immediately take over the mechanical function of the tissue to be replaced (cartilage or cartilage and bone), which means that they are stressable to a limited extent immediately after the operation. Implants of this kind or also transplants, however, have the disadvantage that they must be matched in their shape to the shape of the defect, or that the defect must be cut out or bored out to a predetermined shape prior to the implantation.

It proves that a matching of the implant shape to the shape of the defect which is as exact as possible is advantageous for the healing process. For this reason it is customary in a corresponding surgical operation to cut out the defective location to a recess with a shape which is as definite as possible and to use an implant which has the same shape.

In transplantations of cartilage tissue or cartilage and bone tissue from healthy places to defective places it is, for example, customary to rotate a punch blade with a circular cutting edge into the cartilage tissue and the bone tissue lying below it, to break off the column which is punched out at its base through a wobbling of the blade and to remove it with the blade. This method is used both for the cutting out of defects and for the production of corresponding tissue columns for the transplantation.

A separation of tissue through the above named wobbling of a punch blade is possible only in bone tissue. In other words, this means that this method is restricted to osteochondral "bores" or that defects which affect only the cartilage layer must be deepened to osteochondral bores for the lack of a method for the production of endochondral bores. This disadvantage is not important in the use of tissue columns as transplants which are produced by the same method but is for example a disadvantage in the implantation of cartilage cultivated in vitro.

Furthermore, it proves that columns and openings which are produced in accordance with the named method through punching out and breaking have indefinite base surfaces and heights or depths respectively with relatively large fluctuations, through which the exactness of the fit in the region of this base surface both in transplants and in implants is largely left to chance or must be improved by a plastic mass. For the same reason it is also difficult to orient exactly the surfaces of the transplant or the implant respectively with respect to one another with the known method, which would be important for the success of the operation.

The object of the invention is now to provide an apparatus by means of which endochondral and osteochondral defects can with a minimum enlargement be bored open to endochondral or osteochondral bores with as precisely defined a depth as possible and with as precisely flat a base surface as possible in such a manner that they can be precisely filled with corresponding implants which are cultivated in vitro or which are artificial or else by transplants of a definite shape.

This object is satisfied by the apparatus as it is characterised in the patent claims.

The apparatus in accordance with the invention comprises a combination of a substantially hollow cylindrical sleeve, of which one end is formed as e.g. a circular cutting edge, with a flat borer which is rotatably and axially displaceably arranged in the sleeve. Through pressing in of the cutting edge into the tissue, advantageously only into. the cartilage tissue, a tissue column is punched out which is then cut away and removed through screwing in of the flat borer. In this the boring is done up to the depth of the cutting edge or deeper, with a cut and precisely flat boring base surface arising at each depth. This boring base surface always has the same quality, independently of whether it is situated within the joint cartilage or in the bone tissue. The borer is driven by hand or by a suitable drill.

Figure 5:
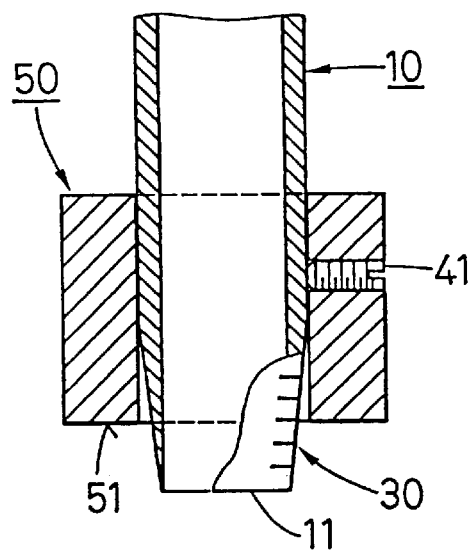
Figure 6:
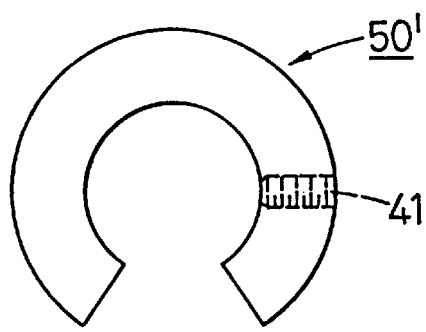
Figure 7:
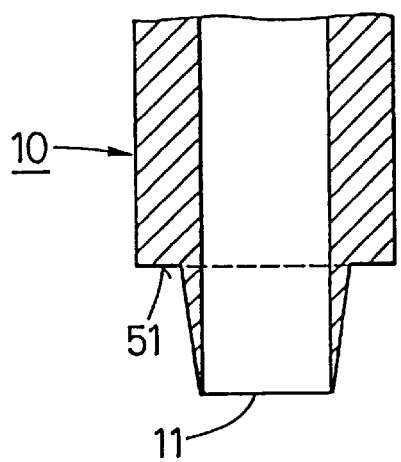

Exemplary embodiments of the apparatus in accordance with the invention will be described in more detail with reference to the following drawings. Shown therein are:

FIG. 1 a first exemplary embodiment of the apparatus in accordance with the invention, sectioned along the axis, FIG. 2 and FIG. 3 further exemplary embodiments of the distal borer end, FIG. 4 a further exemplary embodiment of the borer shaft, sectioned along the axis, FIG. 5 a further exemplary embodiment of the sleeve end with the cutting edge sectioned along the axis, FIG. 6 the abutment piece of FIG. 5 as a plan view, FIG. 7 a further exemplary embodiment of the sleeve end with cutting edge.

FIG. 1 shows a first, exemplary embodiment of the apparatus in accordance with the invention. This consists substantially of a sleeve 10 and a flat borer 20 which is arranged in the sleeve 10. The sleeve 10 is substantially hollow cylindrical, has an internal cavity with a constant diameter at least in the region of its end and runs out at this end to a circular cutting edge 11. The flat borer 20 has a diameter which is matched to the named end of the sleeve 10 in such a manner that it is substantially rotatable without friction at least in this region of the sleeve 10 and is displaceable in the axial direction.

The flat borer 20 is arranged in the sleeve 10 in such a manner that its distal, flat end 21, at which at least two main blades 22 lie (visible in the plan view of the flat end 21), is oriented toward the sleeve end with the cutting edge 11 and can be brought in the region of this cutting edge into positions inside the sleeve 10 and outside the sleeve through axial displacement in conjunction with rotation. For this rotational displacement, for example, a borer shaft 23 is provided which axially extends the borer, which passes through the sleeve and which is provided with a thread 24 which is screwed into a corresponding inner thread in the sleeve 10. Between the thread 24 and the flat borer 20 the borer shaft 23 has a region 25 with a smaller diameter, with the axial extent of this region 25 being at least so large that the cut away material of a bored out tissue column has sufficient room between the sleeve 10 and the thinner region 25 of the borer shaft 23.

At the outer side of the sleeve 10 in the region of the cutting edge 11 and in the region of the opposite end of the borer shaft 23, markings 30 and 31 are provided (for example at spacings of 0.1 mm), on the basis of which, on the one hand, the penetration depth of the cutting edge 11 in the tissue and, on the other hand, the position of the flat, distal borer end 21 relative to the cutting edge 11 can be read off. An addition of the two positions yields an indication of the bore depth reached.

For the production of an endochondral or osteochondral bore the cutting edge 11 is positioned on the tissue surface in the region of the defect, whereas the distal borer end 21 is screwed into the sleeve 10 to such an extent that its distance from the cutting edge 11 corresponds to about the desired bore depth or is greater than the latter. Then the cutting edge 11 is pushed into the tissue, possibly with a slight rotation, in such a manner that it is lowered into the tissue up to the desired bore depth or to a depth which is less than the desired bore depth (for osteochondral bores, for example, up to the boundary between cartilage tissue and bone tissue).

Through the pressing in of the cutting edge 11 into the tissue a tissue column is punched out. The cutting depth can be read off at the sleeve marking 30.

The tissue column which is punched out is cut away through a subsequent screwing in of the flat borer 20, and the material which is bored out is forwarded by the borer into the sleeve 10. The borer 20 is screwed forward at least to a position in which its distal end 21 is flush with the cutting edge 11 (zero point of the marking 31 on the borer shaft 23) in order that at least the entire tissue column which is punched out is cut away and removed. If the boring is to proceed more deeply, then the borer 20 is screwed further forward, with it being precisely guided in the sleeve 10 by the thread 24.

For the screwing in of the borer by hand, a non-illustrated hand grip or at least a thickened and, where appropriate, knurled place is advantageously provided at the part of the borer shaft projecting out of the sleeve 10. Through the flatly arranged main blades 22 of the distal borer end 21 a flat and cleanly cut bore base surface arises at every depth.

The sleeve 10 consists of a corrosion resistant, sterilisable material (e.g. chromium-nickel steel) and has for example a wall thickness of about 1 mm. The cutting edge advantageously has a cutting angle α of about 8°.

The flat borer 20 is, for example, a medical borer which is commercially available and which is made to be a flat borer by a re-grinding of its distal end. Medical borers such as are customary for measures at bones consist of a sterilisable, corrosion resistant material and have a longer twist (smaller twist angle) than steel borers. A clearance of about 2×0.05 mm is provided between the borer 20 and the inner surface of the sleeve 10.

For the initially mentioned uses, borers with diameters of, for example, 3 mm or 5 mm are suitable. Apparatuses with larger bore diameters can however also be realised without further ado. For the initially mentioned uses, an axial borer displacement in the sleeve of about 15 mm is sufficient. The axial length of the entire apparatus amounts, for example, to about 150 to 170 mm.

FIGS. 2 and 3 show two further distal borer ends by means of which the quality of the base surface of the bore can be further improved. Illustrated as a side view in FIG. 2 is the distal end of a flat borer 20', which has a spike 26 at its otherwise flat end side in the region of the borer stem. This spike, which advantageously has an apex angle of about 50°, is driven into the base surface of a bore through the bore movement. Through this it can be ensured that this base surface has no central elevation, such as can arise in the use of a borer in accordance with FIG. 1 through the non-cutting transverse blade 27. A borer with three main blades 22, such as is shown in FIG. 3, can be used for the same purpose. A borer of this kind has no transverse blades.

FIG. 4 shows a further embodiment of that end of the borer shaft 23 which projects out of the sleeve 10 at the side opposite to the cutting edge. In the region of this end a holder piece 40 with a through-going bore 42 is mounted on the borer shaft 23, for example with the help of a fixing screw 41. The bore 42 of the holder piece 40 has a larger diameter on the side facing the sleeve 10 than on the other side, through which an abutment 43 is formed. The abutment 43 is dimensioned in such a manner that the borer or the borer shaft 23 with the thereon mounted holder piece 40 respectively can be pushed forward into the sleeve 10 only to such an extent that the sleeve end arrives at the abutment 43.

Through a corresponding mounting of the holder piece 40 at the borer shaft 23 the bore depth relative to the cutting edge can thus be set prior to the boring, that is, it can be preselected. For the display of the bore depth which is set, a marking 44 is advantageously arranged at the extreme end of the borer shaft 23.

Of course the holder piece 40 can also be mounted firmly (non displaceably) on the borer shaft 23, through which the apparatus is reserved for a definite bore depth (from the cutting edge).

In contrast to the apparatus in accordance with FIG. 1, the apparatus in accordance with FIG. 4 has no thread for the rotational pushing forward of the borer at the borer shaft and at the inner surface of the sleeve. It turns out that the thread, which acts meteringly on the advance of the borer, can be dispensed with. Its guide function is advantageously taken over in this case by a guide ring 28 which is arranged in the sleeve.

FIG. 5 shows a sleeve end with a cutting edge 11 on which an abutment piece 50 is mounted, for example with a fixing screw 41. When this sleeve end is pressed into a tissue surface, the end surface 51 of the abutment piece 50 which is near the cutting edge 11 stops at the tissue surface and thereby limits the depth to which the cutting edge can be pressed into the tissue. Through a corresponding mounting of the abutment piece the pressing-in depth can be preselected and read off at a corresponding marking 30.

For the abutment piece 50, as for the holder piece 40, it holds that it can also be firmly mounted, through which the apparatus is reserved for a definite pressing-in depth.

In order that the abutment piece does not disadvantageously obstruct the view of the surgeon during the pressing in of the cutting edge, it is advantageously not executed as a closed ring about the sleeve, but for example as an open ring. An abutment piece 50' of this kind is illustrated in FIG. 6 as a plan view.

A firmly mounted abutment piece can also be replaced by a corresponding embodiment of the sleeve wall, as is illustrated in FIG. 7. The abutment surface 51 is a step-shaped enlargement of the outer diameter of the sleeve in this case.

What is claimed is:

1. Apparatus for the production of endochondral or osteochondral bores comprising:
    a hollow cylindrical sleeve formed about an axis having a proximal end and a distal end;
    a cutting edge defined by the distal end of the hollow cylindrical sleeve;
    a constant inner diameter formed in the hollow cylindrical sleeve about the axis in the region of the distal end, the constant inner diameter beginning at the cutting edge of the distal end and extending into the hollow cylindrical sleeve;

a borer having a proximal end for rotation from within the hollow cylindrical sleeve;

the borer having a distal end defining a substantially flat cutting surface normal to the axis within the constant inner diameter; and, the borer having displacement along the axis to enable rotation and displacement of the borer relative to the cutting edge inside and outside the constant inner diameter.

2. The apparatus for the production of endochondral or osteochondral bores according to claim 1 and wherein:

the borer projects out of the hollow cylindrical sleeve at the proximal end.

3. The apparatus for the production of endochondral or osteochondral bores according to claim 1 and wherein:

a guide within the hollow cylindrical sleeve extending from the interior of the hollow cylindrical sleeve to the borer.

4. The apparatus for the production of endochondral or osteochondral bores according to claim 3 and wherein:

the guide has a threaded attachment between the borer and the hollow cylindrical sleeve.

5. The apparatus for the production of endochondral or osteochondral bores according to claim 2 and wherein:

a holder piece is mounted to the borer at the proximal end.

6. The apparatus for the production of endochondral or osteochondral bores according to claim 5 and wherein:

the holder piece mounted to the borer at the proximal end has diameter exceeding the hollow cylindrical sleeve whereby the holder piece limits the displacement of the borer along the axis.

7. The apparatus for the production of endochondral or osteochondral bores according to claim 6 and wherein:

the holder piece is removably detachable from the borer.

8. The apparatus for the production of endochondral or osteochondral bores according to claim 1 and wherein:

the cutting edge defined by the distal end of the hollow cylindrical sleeve has an abutment with a limiting surface normal to the axis set back from the distal end towards the proximal end whereby the pressing in depth of the cutting edge is limited.

9. The apparatus for the production of endochondral or osteochondral bores according to claim 8 and wherein:

the abutment is displaceable relative to the cutting edge.

10. The apparatus for the production of endochondral or osteochondral bores according to claim 8 and wherein:

the abutment is removably detachable from the hollow cylindrical sleeve.

11. The apparatus for the production of endochondral or osteochondral bores according to claim 1 and wherein:

the hollow cylindrical sleeve defines markings for indicating the pressing in depth of the cutting edge.

12. The apparatus for the production of endochondral or osteochondral bores according to claim 2 and wherein:

the borer defines markings projecting from the hollow cylindrical sleeve indicating movement of the borer along the hollow cylindrical axis.

13. A method for the production of an endochondral or osteochondral bore comprising the steps of:

providing a hollow cylindrical sleeve formed about an axis having a proximal end and a distal end;

defining a cutting edge at the distal end of the hollow cylindrical sleeve;

providing a constant inner diameter formed in the hollow cylindrical sleeve about the axis in the region of the distal end, the constant inner diameter beginning at the cutting edge of the distal end and extending into the hollow cylindrical sleeve;

providing a borer having a proximal end for rotation from within the hollow cylindrical sleeve, the borer having displacement along the axis to enable rotation and displacement of the borer relative to the cutting edge inside and outside the constant inner diameter;

defining on the borer a distal end defining a substantially flat cutting surface normal to the axis within the constant inner diameter;

pressing the cutting edge of the hollow cylindrical sleeve into tissue a depth which is less than a desired bore depth to create a tissue column with the hollow cylindrical sleeve; and, screwing in the borer to cut away of the tissue column.

14. The method for the production of an endochondral or osteochondral bore according to claim 13 comprising the steps of:

screwing in the borer to cut away all of the tissue column by displacing the borer to the cutting edge.

15. The method for the production of an endochondral or osteochondral bore according to claim 13 comprising the steps of:

defining within the hollow cylindrical sleeve between the borer and the sleeve a region for receiving tissue; and, screwing in the borer to displace the cut away tissue column into the region for receiving tissue.

16. The method for the production of an endochondral or osteochondral bore according to claim 13 comprising the steps of:

screwing in the borer to advance beyond the cutting edge.

17. The method for the production of an endochondral or osteochondral bore according to claim 16 comprising the steps of:

providing a borer which extends beyond the proximal end of the hollow cylinder;

providing markings on the borer beyond the proximal end of the hollow cylinder; and, measuring the displacement of the borer along the axis by observing the marking at the proximal end of the hollow cylinder.

18. The method for the production of an endochondral or osteochondral bore according to claim 13 comprising the steps of:

providing a borer which extends beyond the proximal end of the hollow cylinder; and, attaching an abutment to the cylindrical borer beyond the proximal end of the hollow cylinder to limit the displacement along the axis of the cylindrical borer.

19. The method for the production of an endochondral or osteochondral bore according to claim 13 comprising the steps of:

providing an abutment piece attached to the hollow cylinder at the distal end set back from the cutting edge by a predetermined distance; and, pressing the cutting edge of the hollow cylindrical sleeve into tissue to a depth where the abutment piece limits further penetration of the cutting edge into tissue.

* * * * *